United States Patent [19]

Guitierrez

[11] Patent Number: 5,194,188
[45] Date of Patent: Mar. 16, 1993

[54] PROCESS AND A DEVICE FOR THE DIRECT PRODUCTION OF LIPOSOMES

[75] Inventor: Gilles Guitierrez, Lyons, France

[73] Assignee: Patrinove, Lyons, France

[21] Appl. No.: 656,141

[22] Filed: Mar. 4, 1991

[30] Foreign Application Priority Data

Jul. 5, 1989 [FR] France .................. 89/09275

[51] Int. Cl.$^5$ .................. B01J 13/04; A61K 9/127
[52] U.S. Cl. .................. 264/4.1; 424/450
[58] Field of Search .................. 264/4.1; 424/450

[56] References Cited

U.S. PATENT DOCUMENTS

| | | | |
|---|---|---|---|
| 3,812,056 | 5/1974 | de la Torriente et al. | 264/4.4 X |
| 4,452,747 | 6/1984 | Gersonde et al. | 264/4.1 |
| 4,753,788 | 6/1988 | Gamble | 264/4.1 X |
| 4,895,452 | 1/1990 | Yiournas et al. | 264/4.1 X |
| 4,978,483 | 12/1990 | Redding, Jr. | 264/4.1 X |

FOREIGN PATENT DOCUMENTS 87036 5/1984 Japan .................. 264/4.1

OTHER PUBLICATIONS

McCabe & Smith, Unit Operations of Chemical Engineering, 3rd Ed. (McGraw-Hill, New York) pp. 78-80 (1976).

Primary Examiner—Robert L. Stoll
Assistant Examiner—John M. Covert
Attorney, Agent, or Firm—Pennie & Edwards

[57] ABSTRACT

The method consists of obtaining a preparation liquid by mixing at least one amphiphilic compound and one aqueous medium with an active substance which is soluble or dispersible in the amphiphilic compound or the aqueous medium, setting in motion the preparation liquid and alternately pressurizing and depressurizing the moving preparation liquid. Applications in the preparation of liposomes.

7 Claims, 1 Drawing Sheet

PROCESS AND A DEVICE FOR THE DIRECT PRODUCTION OF LIPOSOMES

The present invention is concerned with the preparation, the manufacture or the production of nanocapsules incorporating an active substance, and more particularly of liposomes.

Liposomes are vesicles, capsules or artificial spheres having a diameter in the order of one hundred nanometres and they are well known in various technical fields, in particular in the pharmaceutical industry. These liposomes are used for incorporating an active substance either into an aqueous medium filling the internal volume of the liposome, or into the wall of the liposome, for transporting said active substance to a site where the active substance will be released and used for various purposes.

By "active substance", is meant in the present invention any matter, product, compound or material capable of being encapsulated by conventional techniques of liposome preparation, and having a use, a technical function or displaying an effect in a process or a method for example of a physical, chemical, physicochemical, therapeutic, pharmacological, biological or biochemical nature.

Amongst the "active substances" as defined above, the following are of a particular interest:
- medicamentous active principles,
- biological materials such as enzymes or fragments of DNA or RNA,
- cosmetic, nutritive products,
- plant protective products,
- agents for modifying the appearance, taste or texture of a foodstuff.

Liposomes are now well known and they have been described and studied in a number of reference books or publications, to which the reader can usefully refer, and amongst which can be quoted:

Liposomes, therapeutic applications, by F. PUISIEUX and J. DELATTRE, published by the Editions Techniques et Documentation—LAVOISIER, and Liposomes in cellular biology and in pharmacology, by Patrick MACHY and Lee LESERMAN, published by the Editions INSERM.

Liposomes in particular have been classified in several categories, and one can distinguish:
- multilayer vesicles, abbreviated as MLV
- large unilayer vesicles, abbreviated as LUV
- small unilayer vesicles, abbreviated as SUV.

The raw materials needed for the preparation or the synthesis of these liposomes are substantially the following:

a) an amphiphilic compound forming the wall of the liposome, for example
- phospholipids, such as lecithin, natural or synthetic phosphatidyl cholines, sphingomyelins, phosphatidyl inositols, phosphatidyl serines, lysophosphatidyl cholines and dicetyl phosphates,
- synthetic or natural surfactants;

b) optionally, a compound for rigidifying the wall of the liposome, for example
- a polycyclic compound comprising a branched chain, such as a sterol of the cholesterol type, phytosterols, acid fluorescein and its esters,
- some aromatic amines,
- some sugars, such as polysaccharides or streptomycin;

c) optionally, a compound conferring a positive or a negative charge to the surface of the liposome membrane, for example
- dipalmitoyl phosphatidyl glycerol for obtaining a negative charge,
- stearyl amine for obtaining a positive charge;

d) optionally an antioxidant for the amphiphilic compound and/or the rigidifying agent, such as $DL-\alpha$-tocopherol;

e) an active substance which can be dissolved in an aqueous medium, in an amphiphilic compound or in an appropriate organic medium.

These different materials are dissolved or suspended in different aqueous and/or organic media, in order to prepare the liposomes according to various methods or pathways using such media.

Without going into the detail and the classification of the different methods of preparation, most of them are carried out in steps.

The first step consists in forming a cellular pseudomembrane and in transforming this membrane into a stable vesicle.

The second step consists in improving the liposomes obtained in the first step and in subjecting them to a fractionation or to a selection involving various physical means, such as a passage through a FRENCH press, a filter, or an ultrasonic treatment. This step ensures in particular the transformation of plurimodal populations of various sized liposomes into small-sized unilayer liposomes.

The third and the last step consists in removing the starting materials which were not used in the encapsulation process, as well as in dissolving or suspending the medium/media, for example through centrifugation or chromatography.

All these techniques have in common several drawbacks, which can be listed as follows:

their overall yield is low, both in terms of the amount of amphiphilic material used in the encapsulation process and in terms of the amount of active substance incorporated into the liposomes; the yield is relatively low and increases accordingly the production time, they involve the use of organic solvents for the dissolution, the suspension or the dispersion operations, which subsequently must be removed; this creates for instance safety and toxicity related problems, besides which thermal treatments must be used requiring energy, the liposomes obtained often display a high level of heterogeneity insofar as their final shape and size distribution are concerned.

The object of the present invention is a new technique for the preparation, the manufacture or the production of nanocapsules, and in particular of liposomes, in a single step and in the complete absence of any dissolving, suspending or dispersing organic medium.

Generally, in the present invention:
- a preparatory liquid is obtained by mixing together at least an amphiphilic compound, an aqueous medium and the active substance, soluble or dispersible in the amphiphilic compound or in the aqueous medium,
- the preparatory liquid is then set into motion, and
- the preparatory liquid set into motion is subjected alternately to high and low pressures.

By low pressure and high pressure, is meant here all pressures respectively beneath and above the static pressure of the preparatory liquid and, in particular, the low pressure can be a partial vacuum. When the preparatory liquid is in motion, these localized pressures are respectively lower and higher than the static pressure of the stream of liquid in motion.

By aqueous medium, is meant here any aqueous phase, whether pure or containing dissolved salts, such as for example an apyrogenic isotonic solution.

Various mechanical means can be used to subject the preparatory liquid in motion to a succession of high and low pressures.

In a preferred embodiment of the invention, use is made of the cavitation phenomenon, which is generally detrimental to the proper functioning and the efficiency of various machines and machine parts such as pumps or propellers. But here and according to the invention, this phenomenon will be generated deliberately and will be controlled in such a manner as to subject the preparatory liquid to a sequence of alternating high and low pressures. As it is well known, cavitation in a liquid refers to the generation within the body of said liquid of localized zones or spaces under low pressure or partial vacuum and of localized zones or spaces under high pressure.

Also, numerous means for achieving cavitation within a liquid are described in the technical literature, and there is no need to recite them all here. Thus, the cavitation phenomenon can be generated by saturating the preparatory liquid with an inert gas and desaturating it, thereby causing the desired cavitation.

In a preferred embodiment of the present invention using the cavitation phenomenon, a stream or a flow of preparatory liquid is circulated in the absence of any inside bulges and the stream is subjected to a cavitation phenomenon through the so-called and well documented "hammer blow", by using appropriate operating conditions and an appropriately designed mechanical system.

Accordingly, a permanent state of cavitation will be achieved, which will generate between the two ends of the stream pressure oscillations, i.e. high pressure and low pressure nodal points, the positions of which are relatively stable. It is precisely in these low pressure nodal points that the liquid undergoes cavitation phenomena.

A device for the direct production of nanocapsules in accordance with the invention comprises:

a treatment tank, a pump, the intake of which is in communication with the tank, a cavitation circuit external to the tank and communicating at one end with the outlet of the pump, means for feeding the tank with preparatory liquid and, means for collecting the nanocapsules obtained.

In accordance also with the invention, the static pressure of the preparatory liquid in motion is set beneath the melting limit of the amphiphilic compounds which are used, and in particular of the lipids in the case of liposomes being prepared.

The operational and mechanical characteristics chosen for the flow of the preparatory liquid subjected to pressure oscillations are dependent upon each other as indicated by the following relation:

$$a = \sqrt{\frac{1}{\rho(1/\epsilon + D/Ee)}}$$

in which:

a = speed of propagation of the pressure oscillations in m/s
$\rho$ = density of the preparatory liquid in kg/m$^3$
$\epsilon$ = bulk modulus of elasticity of said liquid, in N/m$^2$
D = diameter of the stream, in m
e = thickness of the wall channelling the flow, in m
E = modulus of elasticity of said wall in N/m$^2$.

Preferably, the linear speed selected for carrying the invention into effect, is chosen equal to at least 100 m/s in a conduit with a smooth wall, and/or the static pressure of the liquid in motion is chosen equal to at least 100 bars. Such conditions allow the recycling of the preparatory liquid in the low pressure zones of the closed circuit at a high frequency per unit of time.

In order to remain in an aqueous phase, a stabilising milk can be prepared by mixing together a compound for rigidifying the nanocapsule wall, such as a polycyclic compound with a side chain in the case of liposomes, and a dispersive aqueous medium, and this aqueous milk is added to the preparatory liquid.

BRIEF DESCRIPTION OF THE DRAWINGS

A device for the direct production of nanocapsules in accordance with the present invention is now described with reference to the appended drawings, in which.

Figure 3:
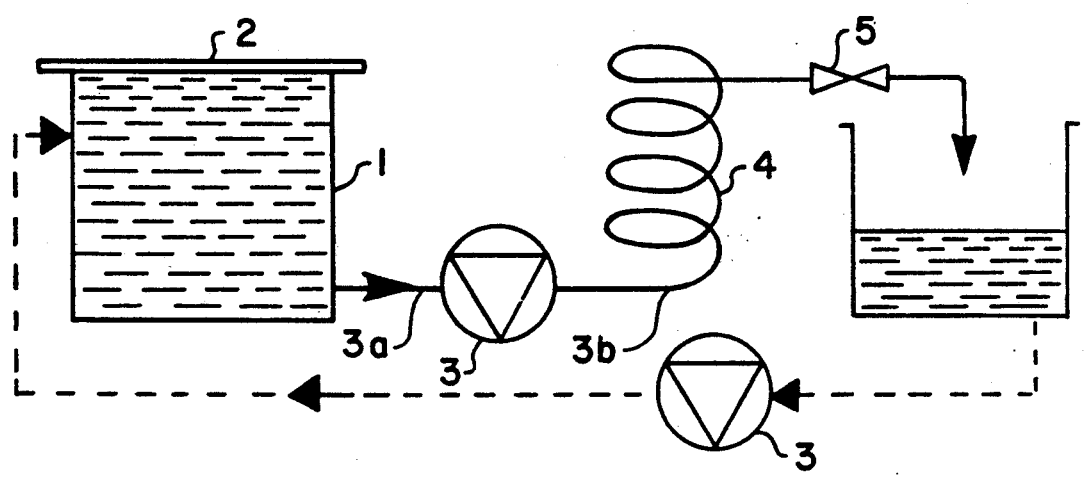
FIG. 3 is a schematic representation of another device in accordance with the invention.

A device according to the invention comprises:

a treatment tank (1), capable of withstanding high pressures, for example pressures in the order of 100 to 200 bars, and which is provided with a lid (2) capable of being fastened releasably and hermetically on tank (1); this lid (2) is used both to feed the tank in preparatory liquid and optionally to discharge from the same the suspension of nanocapsules obtained, a pump (3), the inlet (3a) of which is in communication with the bottom of tank (1), and a cavitation circuit (4) outside tank (1), in communication at one end with the outlet (3b) of the pump and at the other end, via a pressure reducing valve (5), with an inlet (la) for recycling into the tank (1) containing the batch of preparatory liquid. The recycling operation is optional, and a system not provided with this facility is illustrated in FIG. 3.

Figure 1:
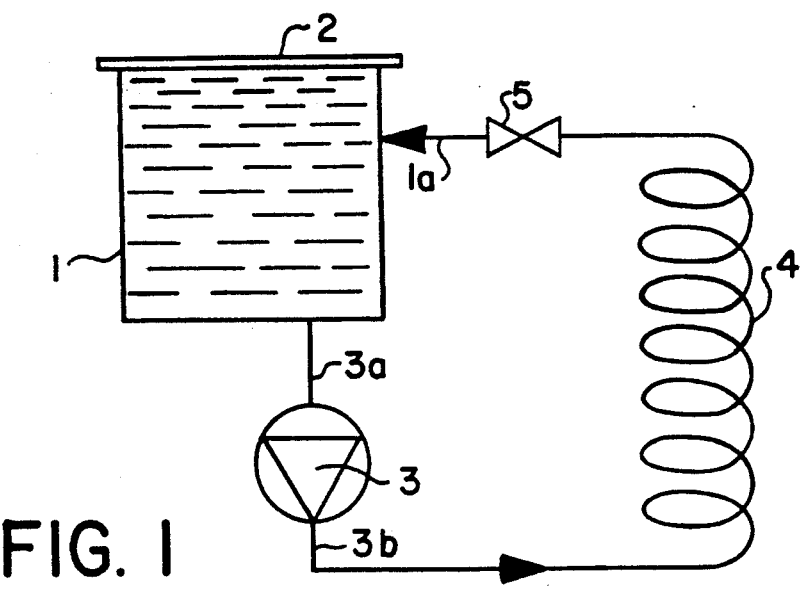
FIG. 1 is a schematic representation of a device according to the invention.
Figure 2:
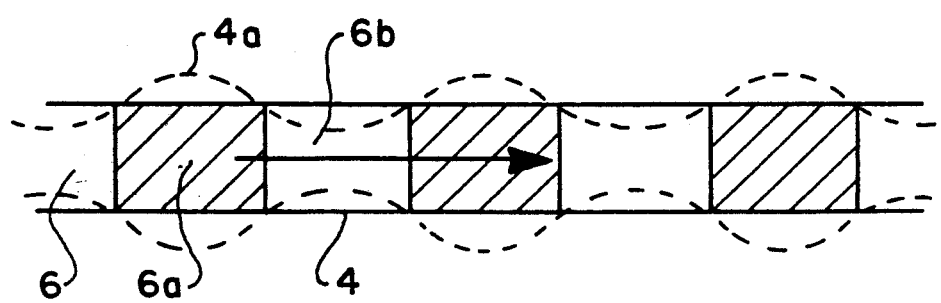
FIG. 2 is a schematic representation of the flow of preparatory fluid subjected to a controlled cavitation phenomenon.

While the lid (2) of the above described apparatus for carrying out the method of the invention is open, tank (1) is filled to the top with the preparatory liquid obtained as described previously and optionally with the stabilizing milk also discussed above. Then the lid (2) is closed, so that the subsequent operations may be carried out in the complete absence of air. The operational conditions and/or mechanical parameters of the device of FIG. 1 are set as discussed previously and then pump (3) is actuated to produce and control the cavitation phenomenon in loop (4). As shown in FIG. 2, where the cavitation circuit (4) is drawn straight and developed, oscillations of high pressure and of low pressure in a stationary state appear inside the stream (6) of preparatory liquid in motion, respectively at (6a) and (6b), which results in the generation of bulges and of depressions in the wall (4a) of the circuit (4) shown in phantom in FIG. 2, when said wall (4a) has a measure of elasticity, whilst being capable of withstanding pressure. In the nodal points of low pressure (6b), evaporation of the aqueous medium takes place as liposomes are simultaneously formed, and in the nodal points of high pressure (6a) the incorporation of the lipophilic products takes place.

In accordance with the invention, a gas can be dissolved beforehand in the preparatory liquid, i.e. before the latter is set into motion.

Some gases such as for example helium have a low solubility in water and can therefore produce bubbles more readily. Also, the greater the pressure difference between the nodal points at high pressure (6a) and at low pressure (6b), the bigger the bubbles generated.

The overall number of high pressure and low pressure zones in the cavitation circuit increases in direct proportion with the length of said circuit: the higher their number, the narrower the distribution histogram of the nanocapsules.

In the experiments, a device according to FIG. 1 was used, which had the following characteristics:

the treatment tank (1) had a volume amounting to 18 liters;

the pump (3) had a nominal output of 950 liters/hour and a pressure at its outlet of 175 bars;

the tube forming the loop (4) was 8 meters long and it was capable of withstanding a pressure of 250 bars, while the volume of circuit (4) and of pump (3) amounted to 2 liters.

Liposomes of vitamin E and of trypan blue were prepared using a device such as described above.

EXAMPLE 1

In the case of liposomes of vitamin E and of the above described device having an overall volume of 20 liters, the following amounts of raw material were used:

| | |
|---|---|
| soya phosphatidyl choline | 1000 g |
| cholesterol | 80 g |
| DL-α-tocopherol | 100 g |
| tocopherol acetate (vitamin E) | 100 g |
| sodium ascorbate | 2 g |
| apyrogenic water | complete to 20 liters |

The operating conditions were the following:

| | |
|---|---|
| pressure at the outlet of the pump | 150 bars |
| output of the pump | 600 l/hr |
| room temperature | |

After 5 minutes, a sample was taken which showed that 50% of the lecithin was not yet spherically shaped, but this proportion decreases in the course of time: after 40 minutes, the yield amounted to virtually 100%.

EXAMPLE 2

It this example, trypan blue liposomes were prepared. The same operating conditions were used, except that the vitamin E or tocopherol acetate were replaced by the same amount of trypan blue.

The liposome solution finally obtained showed that the amount of colouring agent encapsulated in the hydrophilic phase amounted to 46%. The colouring agent which is not encapsulated is removed by chromatography on a Sephadex G 50 resin. After a 24 hr elution of the liposomes, it was found that the latter had retained 100% of their colouring agent, which demonstrates their stability and their imperviousness.

Finally, the process according to the invention provides the following important additional advantages. Firstly, this process is not dependent upon the transition temperature of the amphiphilic compound, which offers the possibility of working at any temperature, for example in the vicinity of the room temperature and therefore of processing substances which are temperature sensitive and subject to degradation by heat.

The examination of the nanoparticles and in particular of the liposomes obtained according to the invention indicates that their size and their distribution histograms are little affected by temperature.

Finally, the cavitation phenomenon offers the possibility of operating only in the presence of the vapour of the preparatory liquid or in the presence of an inert gas which was dissolved deliberately, i.e. in a generally inert atmosphere, which cannot oxidize those raw materials sensitive to an oxidative degradation.

I claim:

1. A process for direct preparation of lipsomes incorporating an active substance, characterized in that a preparatory liquid is obtained by mixing together at least one amphiphilic compound, an aqueous medium and the active substance, dissolved or dispersed in the amphiphilic compound or in the aqueous medium, in that the preparatory liquid is set into motion as a stream of liquid having no inside bulges were a cavitation phenomenon is generated by alternatively pressurizing and depressurizing the stream of liquid.

2. A process according to claim 1, characterized in that the static pressure of the preparatory liquid set in motion is adjusted beneath the melting limit of the amphiphilic compounds added to the liquid.

3. A process according to claim 1, characterized in that the operational and the mechanical characteristics chosen for the flow of the preparatory liquid subjected to pressure oscillations are dependent upon each other as indictaed by the following relation:

$$a = \sqrt{\frac{1}{\rho(1/\epsilon + D/Ee)}}$$

in which:
 a=speed of propagation of the pressure oscillations in m/s
 $\rho$=density of the preparatory liquid in kg/m$^3$
 $\epsilon$=bulk modulus of elasticity of said liquid, in N/m$^2$
 D=diameter of the stream, in m
 e=thickness of the wall channelling the flow, in m
 E=modulus of elasticity of said wall in N/m$^2$.

4. A process according to claim 1, characterized in that the cavitation phenomenon is obtained by a flow of the preparatory liquid having a linear speed of at least 100 m/s inside a conduit with a smooth wall.

5. A process according to claim 1, characterized in that the preparatory liquid is circulated in a circuit comprising a pump, a treatment tank and a cavitation circuit located outside the tank.

6. A process according to claim 5, characterized in that the circuit is open or closed.

7. A process according to any one of the preceding claims, characterized in that the preparatory liquid contains a gas, which was previously dissolved.

* * * * *

UNITED STATES PATENT AND TRADEMARK OFFICE
CERTIFICATE OF CORRECTION

PATENT NO. : 5,194,188

DATED : March 16, 1993

INVENTOR(S) : Gilles Gutierrez

It is certified that error appears in the above-indentified patent and that said Letters Patent is hereby corrected as shown below:

On the title page, under item [19] and item [75], "Guitierrez" should read --Gutierrez--.

Signed and Sealed this

Fourth Day of January, 1994

*Attest:*

BRUCE LEHMAN

*Attesting Officer*     *Commissioner of Patents and Trademarks*